United States Patent
Craen et al.

(10) Patent No.: US 8,366,001 B2
(45) Date of Patent: Feb. 5, 2013

(54) CALIBRATION METHODS FOR IMAGING SYSTEMS AND IMAGING SYSTEMS USING SUCH

(75) Inventors: Pierre Craen, Embourg (BE); Olivier Jacques-Sermet, Lyons (FR); Bruno Berge, Lyons (FR)

(73) Assignee: Varioptic S.A., Lyons (FR)

(*) Notice: Subject to any disclaimer, the term of this patent is extended or adjusted under 35 U.S.C. 154(b) by 712 days.

(21) Appl. No.: 12/540,026

(22) Filed: Aug. 12, 2009

(65) Prior Publication Data
US 2010/0040355 A1  Feb. 18, 2010

Related U.S. Application Data

(60) Provisional application No. 61/088,904, filed on Aug. 14, 2008.

(51) Int. Cl.
*G06K 7/10* (2006.01)

(52) U.S. Cl. .......... 235/454; 235/438; 235/470; 348/36; 348/49; 348/222.1; 348/345

(58) Field of Classification Search .................. 235/454, 235/438, 470; 348/36, 49, 222.1, 345
See application file for complete search history.

(56) References Cited

U.S. PATENT DOCUMENTS

| 7,245,440 | B2 | 7/2007 | Peseux et al. | |
|---|---|---|---|---|
| RE39,874 | E | 10/2007 | Berge et al. | |
| 7,573,646 | B2 | 8/2009 | Craen et al. | |
| 2004/0100573 | A1* | 5/2004 | Nonaka | 348/345 |
| 2006/0126190 | A1 | 6/2006 | Berge et al. | |
| 2007/0002455 | A1 | 1/2007 | Berge et al. | |
| 2007/0133103 | A1 | 6/2007 | Stempel et al. | |
| 2007/0177276 | A1 | 8/2007 | Liogier D'ardhuy et al. | |
| 2007/0179200 | A1 | 8/2007 | Liogier D'Ardhuy et al. | |
| 2007/0179201 | A1 | 8/2007 | Maillard et al. | |
| 2007/0199454 | A1* | 8/2007 | Bae et al. | 100/90 |
| 2008/0030870 | A1 | 2/2008 | Bruno et al. | |

FOREIGN PATENT DOCUMENTS
EP  1662276 A1  5/2006

* cited by examiner

*Primary Examiner* — Allyson Trail
(74) *Attorney, Agent, or Firm* — Osha Liang LLP

(57) ABSTRACT

A method for calibration in the field of imaging systems and imaging systems using the method for calibration. In particular, the method involves calibration in the field of open loop variable focus imaging systems and methods for calibration in the field of imaging system having a variable optical parameter.

22 Claims, 8 Drawing Sheets

CALIBRATION METHODS FOR IMAGING SYSTEMS AND IMAGING SYSTEMS USING SUCH

CROSS-REFERENCE TO RELATED APPLICATIONS

This application claims benefit of U.S. Provisional Application 61/088,904, filed on Aug. 14, 2008, entitled "REAL TIME CALIBRATION METHODS FOR IMAGING SYSTEMS," and in the name of Pierre Craen et al.

BACKGROUND

1. Field of the Disclosure

The invention concerns calibration methods for imaging systems and more especially methods for calibration in the field of image capture systems. It further concerns imaging systems implementing such calibration methods.

2. Background of the Invention

Variable focus image capture systems are becoming increasingly integrated in picture acquisition devices and data capture devices. Such devices include but are not limited to 1D and 2D barcode readers, machine vision image capture devices, fingerprint or iris recognition systems. Focusing ability is becoming a must-have feature for those image or data capture devices. For instance, 2D barcodes are becoming increasingly common, and their decoding requires imaging devices instead of laser scanners.

Such a variable focus image capture system usually comprises a camera module composed of a CMOS or CCD sensor (matrix or linear), an imaging lens module, a focusing actuator, and a distance measurement device.

When the user of the system wants to take a picture of an object, the distance measurement device determines the distance from the system to the object and sends the right command to the actuator so that the optical module can focus onto the object and therefore maximize image quality. Also, using this distance measurement device maximizes aggressiveness, i.e., the time to capture the data and to process it, in other words the time to decode the image information. Typical distances range from a few centimeters to infinity and aggressiveness is typically less than ~0.2-0.4 sec.

FIG. 1A illustrates a schematic view of a 2D bar code reader 100. It comprises a camera module (CM) 101 characterised by an optical axis ($\Delta$) and a given field of view ($\theta_{FOV}$). The camera module 101 comprises a sensor 102 and a lens arrangement 103 settled in a housing 104. The lens arrangement 103, schematically represented on FIG. 1A, comprises an electrically controlled optical device (not represented on FIG. 1A), for example a liquid lens, for adjusting the focus of the device. The focus is adjusted as a function of the measured distance of the barcode 105. The imaging system further comprises a driver 106 for applying a predetermined electrical signal to the electrically controlled optical device which is a function of the measured distance, It further comprises processing means 107, e.g. an Imaging Signal Processor, usually called "ISP", that will process the image and control the sensor parameters. A user interface 108 is connected to the processing unit 107 via a decoder 109. A nearly collimated laser beam 110, emitted by a laser source 111, and making a given angle with the optical axis of the imaging system, crosses the field of view of the imaging system in such a way that the image of the laser spot reflected from a barcode located at far and near distances (B and A points respectively) will move over the field of view of the imaging device (B' and A' points in the sensor plane). The image of the laser spot will thus be translated over the sensor height or width. In measuring the position of the centroid of the laser spot on the sensor, the distance can be computed based on a preliminary calibration. A memory 112 stores the parameters of the calibration. A power supply 113 provides the electrical power to the different elements of the system.

In such applications, focusing speed, or time to focus, is a critical parameter. Conventional auto-focus methods, where the actuator command is dynamically optimized depending on sensor feedback, cannot be used because such closed-loop driving requires several steps (images acquisition) to achieve focusing through the commonly called full scan search, leading to a very long time to focus not suited to cited applications.

Thus, the use of an external device is required to determine directly the right command to send to the actuator. In the case of a focusing lens module, this external device is the distance measurement device.

When the optical module is used in addition to a distance measurement device, it is possible to adjust the module to focus on the object that is at the measured distance. This also refers to what is commonly called "open-loop" systems, wherein no feedback about an output is taken into account to generate the output, and wherein an external input data can be used, for example a distance measurement, to generate the output. It leads to extremely fast time to focus as only one command on the actuator is required. In comparison, a close-loop system based on an autofocus loop requires several steps, including the acquisition of images at a fixed frame rate of typically 15 to 60 Hz, and takes much more time—typically 0.5 to 1 second.

On the other hand, open-loop driving of the module requires storing the distance/actuator command relationship in the actuator's driving system, which is usually stored in the memory chip 112 or in a computer.

Let us take the example of a liquid lens, which is a voltage-driven focusing actuator. Such liquid lens is described for example in European Patent Application EP 1662276 in the name of the applicant. It comprises a refractive interface between first and second immiscible liquids that is movable by electrowetting. More precisely, as detailed in the above mentioned reference, a liquid lens often comprises two transparent windows, wherein said windows can be fixed lenses in some embodiments, arranged in parallel and facing each other, and delimiting, in part, an internal volume containing two immiscible liquids with different optical indices. Where the two liquids meet they form an optical interface in the form of a meniscus, which can have a number of different shapes. The liquids have substantially equal densities, and one is preferably an insulating liquid, for example comprising oil and/or an oily substance, and the other is preferably a conductive liquid comprising for example an aqueous solution.

The distance/actuator command relationship for such a liquid lens is shown in FIG. 1B. For a liquid lens, the command is voltage; for mechanical actuators it can be current. This context can be applied to any kind of command. As it is shown on FIG. 1B, the relationship is linear, or quasi linear, for a focusing distance from Distance 1 to Distance 2. The voltage values to reach Distance 1 and Distance 2 depend on every single actuator. As the response is linear, only two values are needed in this particular case to completely determine the relationship The distance/actuator command relationship is stored as a look-up table, in every unit that includes the variable focus module, at the end of production, thanks to a calibration process. But, during the lifetime of the unit, this initial calibration may not be relevant anymore. Indeed, if the characteristics of the unit change over time, the look-up table may have to take these changes into account so that the best performance is guaranteed over time. Further, the look-up table may vary over the working temperature range of the device (e.g. −20 to +60° C. for industrial devices). In such cases a temperature sensor is embedded in the system and its output is used to adjust the values of the look-up table.

A problem to solve is the calibration of each individual unit at the end of production, as well as periodical recalibration during the lifetime of the product. Since it is too costly to send the unit back to the manufacturer for recalibration, a calibration system that is included in the device is a big advantage.

SUMMARY

According to a first aspect of the present invention, there is provided a method for calibration in the field of an open loop variable focus imaging system, said imaging system comprising a sensor, a lens arrangement with an electrically controlled focal length optical device for adjusting the focus as function of a distance measurement of an object to be imaged, a driver for applying a predetermined electrical signal to the electrically controlled optical device, said signal being related to the measured distance by a function whose parameters are pre-recorded, said method comprising:

for at least two distances, determining for each distance the value of the electrical signal to be applied to get the best image contrast measurement of the image of an object positioned at said distance, updating the parameters of the function between the electrical signal to be applied and the measured distance using the said at least two values.

According to another embodiment of the first aspect of the present invention, there is provided a method for calibration in the field of an open loop variable focus imaging system, said imaging system comprising a sensor, a lens arrangement with an electrically controlled focal length optical device for adjusting the focus as function of a distance measurement of an object to be imaged, a driver for applying a predetermined electrical signal to the electrically controlled optical device, said signal being related to the measured distance by a function whose parameters are pre-recorded, said method comprising:

recording, over the life time of the imaging system, values of contrast image measurements for images of an object as function of the distance of said object, determining when a significant loss of contrast has occurred, and applying a correction in the parameters of the function as function of said loss of contrast.

The present invention also relates to an open loop variable focus imaging system incorporating the calibration method according to the first aspect.

According to second aspect, the present invention relates to a method for calibration in the field of an imaging system comprising a sensor, a lens arrangement with an electrically controlled optical device for adjusting a given optical parameter as function of an external measured parameter, a driver for applying a predetermined electrical signal to the electrically controlled optical device, said signal being related to the external measured parameter by a function whose parameters are pre-recorded, said method comprising:

providing a calibration system with a light emitting system to form an image of a light source on the sensor of the imaging system through the lens arrangement of said imaging system, analysing the images of the light source formed on the sensor for at least two values of the applied electrical signal on the electrically controlled optical device, determining, for each value of said applied signal, the value of the optical parameter from the analysis of the image formed on the sensor, and, updating the parameters of the function between the electrical signal to be applied and the external measured parameter using the said at least two values.

The present invention also relates to an open loop variable focus imaging system incorporating the calibration method according to the second aspect.

DETAILED DESCRIPTION

Calibration Method and Imaging System Using Such According to the First Aspect of the Invention According to a first aspect, the invention is directed to a calibration system that can be seamlessly integrated to an imaging system with no extra piece of hardware, that can be performed at any time and that does not necessarily need an action of the end user. In the present description, the expression "calibration in the field" will be used to designate such a calibration method that can be performed at any time and that does not necessarily need an action of the end user. The invention according to the first aspect of the invention encompasses different embodiments of a method of calibration in the field of an open loop variable focus imaging system and also open loop variable focus imaging systems using such.

Figure 2A:
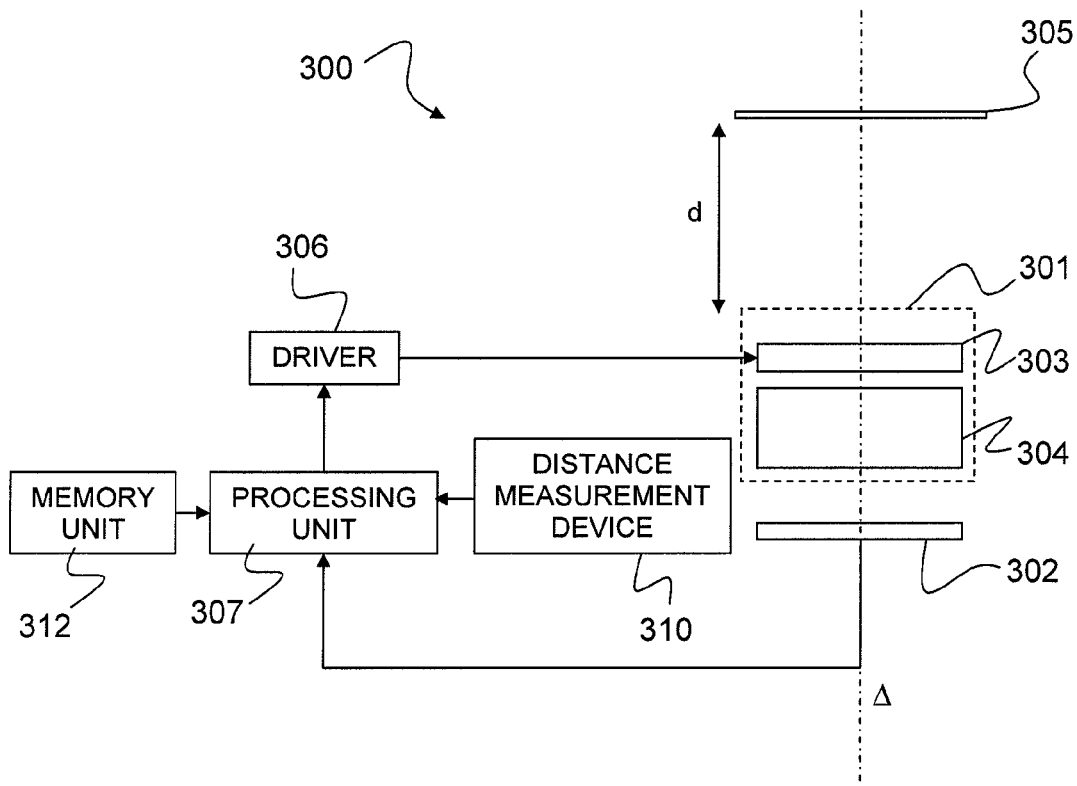
FIG. 2A illustrates an open loop variable focus imaging system according to one embodiment of the first aspect of the invention.

FIG. 2A illustrates schematically an open-loop variable focus imaging system 300 according to one embodiment of the first aspect of the invention. Imaging system 300 comprises a sensor 302, an optical lens arrangement 301 having an optical axis (Δ) and including an actuator 303, for example an electrically controlled focal length optical device. Such electrically controlled focal length optical device may be for example a variable focal length liquid lens as described in European patent application EP1662276, the content of which is hereby incorporated, and fixed optics 304 comprising at least one lens. Various embodiments of such a variable liquid lens are described in EP1662276.

Such a variable focus liquid lens comprises a fluid chamber defined by two parallel windows facing each other, and a body to which the windows are fixed. The windows are preferably transparent plates formed of an optical transparent material such as glass, or may be lenses. The fluid chamber contains two immiscible liquids of similar density and having different optical indices, which form an optical interface in the form of a meniscus. One of the liquids is preferably an insulating liquid, for example comprising oil and/or an oily substance, and the other is preferably a conductive liquid comprising, for example, an aqueous solution. The liquid lens also comprises a cap and a gasket that is sandwiched between the cap and the body ensuring the tightness of the lens structure. The conductive liquid is in contact with an electrode formed by the cap, and the liquid-liquid interface contacts a conical part of the body that comprises an insulated electrode. Through electrowetting phenomena it is possible to modify the curvature of the liquid-liquid interface, according to the voltage V applied between the electrodes formed by the cap and the body. For example, the curvature changes from the concave initial shape to the convex shape. Thus, a beam of light passing through the fluid chamber will be focused to a greater or lesser extent according to the applied voltage.

The actuator 303 of the optical lens arrangement 301 is electrically controlled by a driver 306 that applies driving voltages such that the focal length of the optical assembly 301 is changed. Imaging system 300 further comprises a processing unit 307 that computes the electrical command applied by the driver 306 to the actuator 303. This electrical command depends on the position of the object 305 located at a distance d from the imaging system 300 on the optical axis A. The processing unit 307 may comprise image analysis means and calculating means. The processing unit 307 uses as inputs a distance information given by a distance measurement device 310 and calibration data stored in the memory unit 312, to compute the required electrical command and send it as an output to the driver 306. The driver 306 then applies this predetermined electrical signal to the electrically controlled optical device 303. Electronic components 302, 306, 307, 310 and 312 are powered by an ad hoc power supply, not shown on the FIG. 2A.

The calibration method according to the first aspect of the invention may comprise the determination of the relationship between the distance, corresponding to the distance of an object to be imaged to the imaging system that is measured by a distance measurement device, and the command to send to the actuator enabling the variable focusing. In fact, the actual distance is not important in the calibration method: what is important is to link the distance value given by the measurement device to the command value sent to the actuator.

According to a one embodiment, the calibration method may comprise a closed-loop focusing operation performed in parallel to the distance measurement operation in order to establish the above described relationship between the distance and the command for driving the actuator. Closed-loop focusing may be based on a strategy that scans the full distance range to find the best focus position.

Figure 2B:
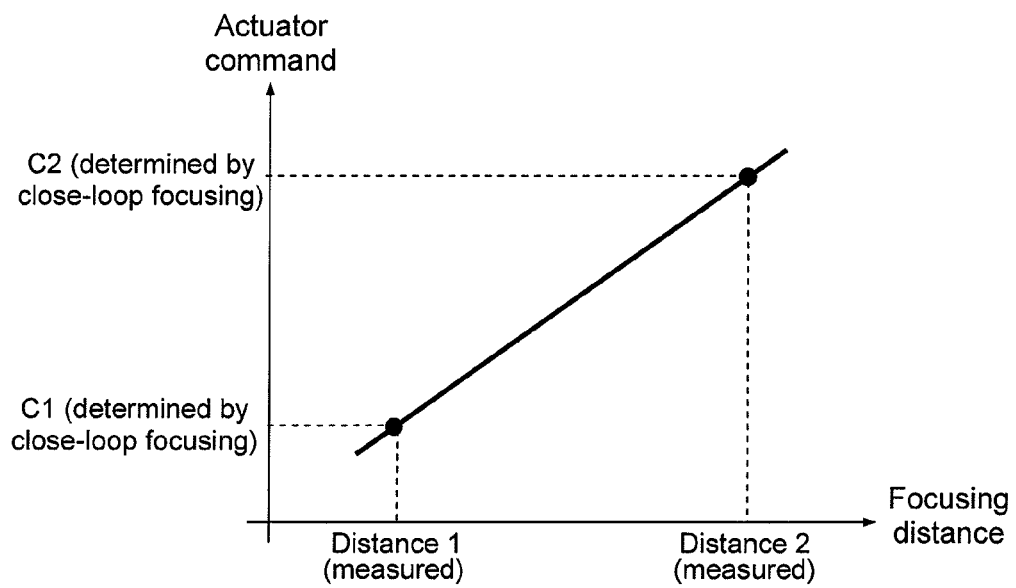
FIG. 2B illustrates the actuator command determined after a calibration method according to one embodiment of the first aspect of the invention, where actuator commands C1 and C2 have been determined by the focusing loop illustrated in FIG. 3.

In the case of a linear actuator, showing a linear or quasi linear distance/actuator command relationship, only two values are necessary to fully determine this relationship, as illustrated by the graph in FIG. 2B.

Figure 3:
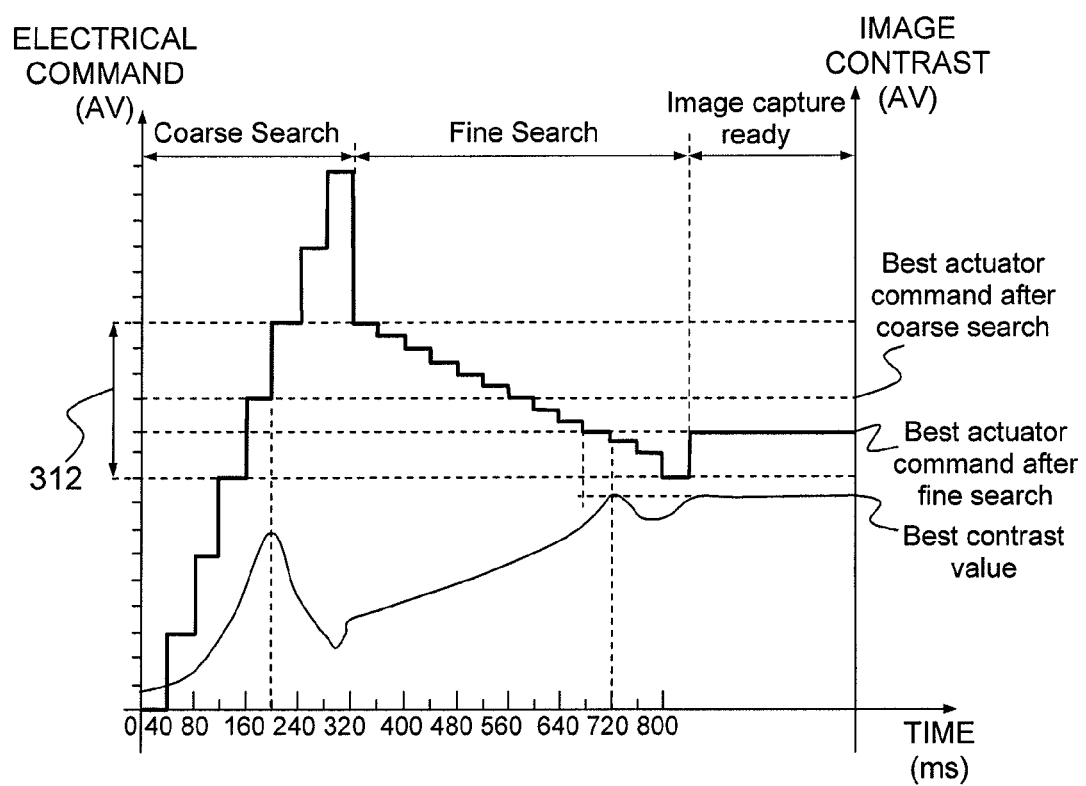
FIG. 3 is a graph illustrating the application of the actuator command to a liquid lens according to one embodiment of the calibration method according to the first aspect of the invention.

FIG. 3 is a graph showing one preferred embodiment of the calibration method according to a first aspect of the invention, wherein such a close-loop focusing strategy is used together with a distance measurement operation. The focusing strategy applies coarse then fine steps to the actuator. At each step, a picture is taken and its degree of sharpness is computed. The system analyses the evolution of the sharpness and applies to the actuator the command for which the sharpness is maximal. In order to determine a point of the graph presented in FIG. 2B, and corresponding to the couple (focusing distance, actuator command), the calibration method is to perform in parallel and as simultaneously as possible:
 a measurement with the distance measurement device, that gives the "distance" value;
 a closed-loop focusing, that gives the "actuator command" value to get a sharp picture.

In the embodiment of the calibration method illustrated in FIG. 3, the close-loop auto-focusing may be based on image contrast measurement. The whole process requires several steps, for example 20 steps as shown in FIG. 3, where step duration depends on the sensor frame rate, typically 40 ms at 25 frames per second. At each step, the sensor output is processed by the ISP to calculate the contrast of the image. This contrast value, in arbitrary units, is greater when the image is sharper and reciprocally. The goal of the auto-focus loop is to find the actuator command for which the contrast is the greatest, by applying different commands to the actuator and measuring the resulting image contrast. In the example shown, the loop consists in two successive steps:
 a coarse search, where large steps, for example seven steps, are applied to the actuator to scan the whole focusing range;
 then a fine search, around the best position found by the coarse search, with small steps, for example thirteen steps, is performed to maximize contrast value.

In this embodiment, the best actuator command is for example determined in about 800 ms. Depending on the sensor frame rate and on the auto-focus strategy, typical times range from 500 to 1000 ms.

In order to determine the distance/actuator command relationship, at least two couples (focusing distance, actuator command) are needed, that is the above described operations of distance measurement and close-loop focusing have to be performed for two objects located at two different distances (for instance, a few centimeters and a few meters), as illustrated for example on FIG. 2B wherein two points are sufficient to determined the linear relationship of a linear actuator.

Thereafter, the table that links the value given by the distance measurement device and the command sent to the actuator can be stored in the imaging device, in a memory unit, and then used at each focusing operation: when the user asks the system to focus on a target, the distance measurement device measures the distance to the target and uses the lookup table to determine the command to send to the actuator.

The method according the first aspect of the present invention is also applicable to actuators that have a non-linear response, with a higher actuator command sampling (more than two points). The sampling depends on the complexity of the response. For example, a second degree polynomial response will require 3 points and not more.

One advantage of the invention according to this first aspect is that no extra external component is needed in the imaging system since all required components are already present in the system.

Described embodiments of the calibration method according to the first aspect of the invention can be used in several configurations:

- at the end of production, to calibrate the unit by focusing on two targets at different distances;
- if the user feels his system is missing focus which leads to a loss of aggressiveness, for example decoding aggressiveness in the case of barcode reader applications, and estimates it needs to be calibrated again, he can decide to perform a recalibration by launching the calibration process based on the present invention and by using his device towards objects at two different distances;
- if the focusing strategy is not pure open-loop but a mix between open and closed loop, for example using the distance measurement to place rapidly the actuator close to the best position, and then refining this position thanks to closed-loop steps around this position, then the present invention can be applied at each use of the device.

According to a further embodiment of the calibration method, the recalibration can be performed either at each use, or only when the difference between the initial calibration and the actual measurement is higher than a given threshold.

In a further embodiment of the calibration method statistics of previous image captures may be used. According to such an embodiment, the imaging system may be used in pure open-loop and may be calibrated once at the end of its production. Therefore, each time an image is captured, the distance sensor gives the distance information to the processing unit (for example an ISP) which computes the required actuator command. Once the picture is taken, the processing unit can compute the contrast of the picture, which can lead to a measurement of the sharpness of the picture. At the beginning of the life of the product, the obtained contrast values are generally as high as specified by the manufacturer, but as the system calibration changes over time, the average value of contrast values is decreasing. Indeed, if for example the object distance is 20 cm and the actuator calibration has changed by 1 dioptre, the actual focusing distance is then 25 cm when the measured distance is 20 cm. So the picture is not taken at the best object plane, which results in a loss of contrast. The calibration method principle consists in recording the couple (measured distance; picture contrast) values over the lifetime of the product and to compute their average value. When a significant amount of data has been recorded, for at least two distances, the loss of contrast versus time can be matched with the evolution of the actuator predicted by the manufacturer. For example, if the manufacturer knows that a 10% loss of contrast at close distance is linked to a 1 dioptre change, the 10% threshold in averaged contrast values can trigger a 1 dioptre shift in the look-up table. This embedded recalibration system thus allows compensating the drift of the actuator during its lifetime.

Such an embodiment of the calibration method is particularly well adapted to a liquid lens actuator that may drift slightly or vary with temperature but is very insensitive to shocks.

Figure 4A:
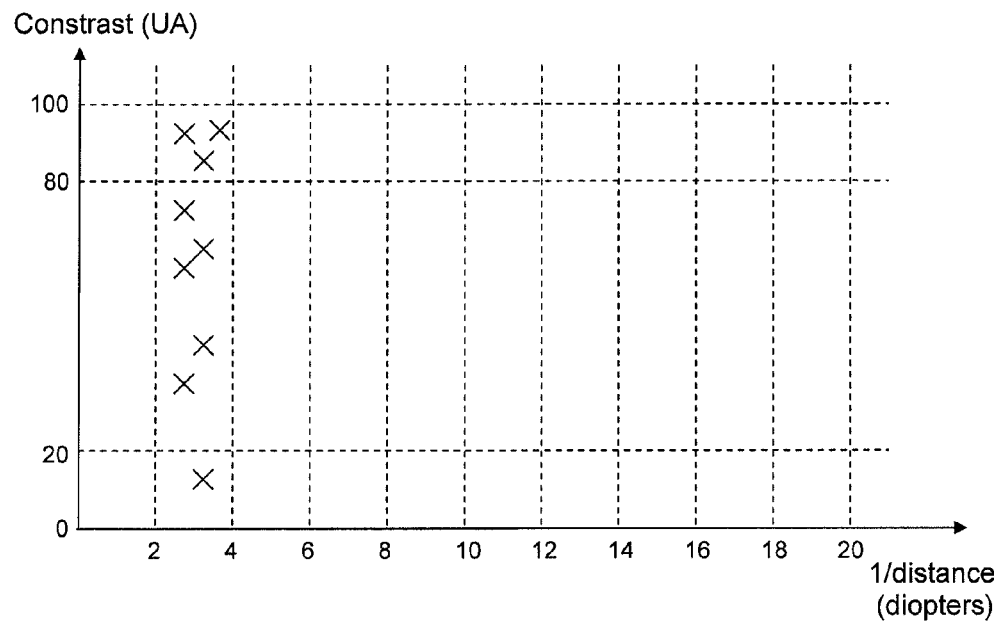
FIGS. 4A, 4B, and 4C illustrate another embodiment of the calibration method according to the first aspect of the invention.
Figure 4B:
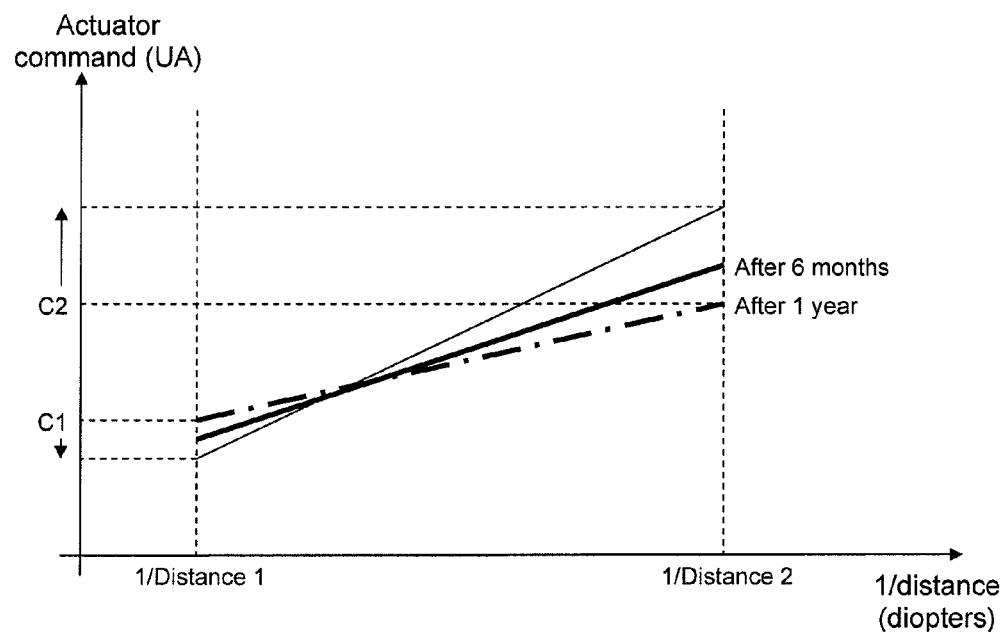
Figure 4C:
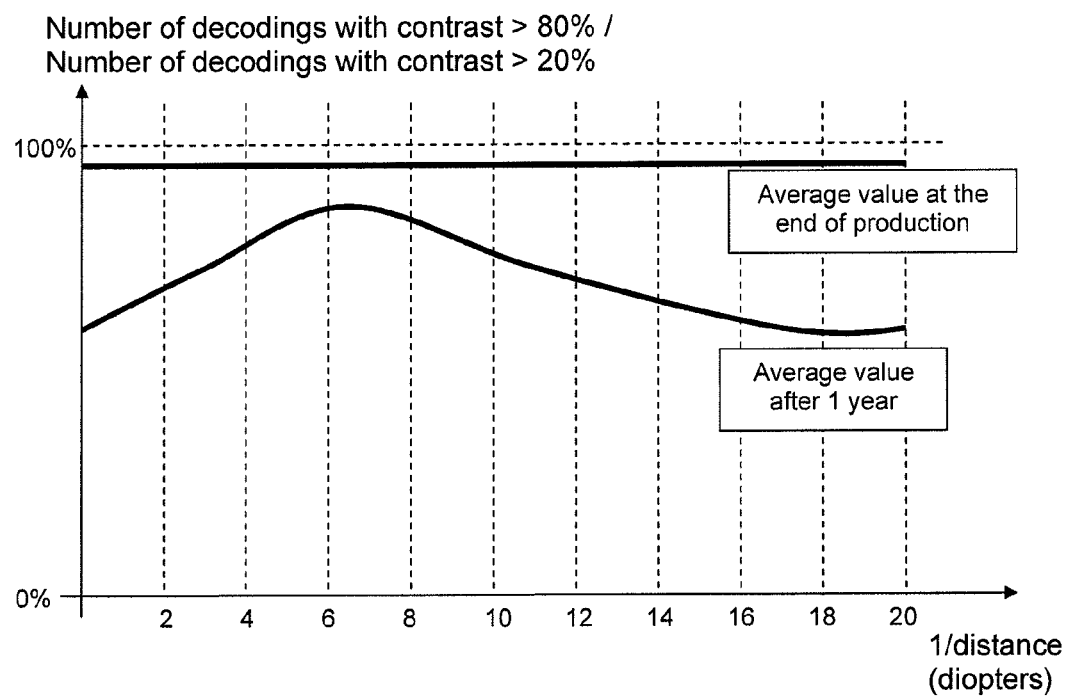

FIGS. 4A to 4C illustrate in more details such an embodiment of the calibration method according to the first aspect of the invention that is particularly well suited to a linear actuator such as liquid lenses. In this embodiment, the imaging system is for example a camera module having a variable focal length with a focal range of 20 dioptres, leading to an ability to focus onto objects from infinity to 5 cm. During the lifetime of the product, it is very likely that the whole focusing range may be used when the user takes pictures of objects located at various distances.

The calibration method according to this embodiment may be based on the recording of information, for example at each bar code decoding in the case of barcode reader applications, for different object distances, as shown on FIG. 4A. The distance range is for example divided in ten zones, each with an equal length of 2 dioptres. The distance measurement device gives the distance value to the actuator, and then the sensor acquires a picture and decodes its information. Plus, it computes the contrast, for example as described above. For each of these zones, the number of decodings with contrast higher than 20% (to eliminate pictures of objects that are not bar codes) and the number of decodings with contrast higher than 80% (representative of accurate focusing at the right distance) are stored in a memory chip. The values of the 80% and 20% threshold are examples only and depend on the entire system. This system requires memory space in the chip for two values for each distance zone. In this example, 20 numbers need to be recorded. Then, the ratio between these two values is computed, as illustrated on FIG. 4C. At the end of production, with a freshly calibrated unit, it is expected that the contrast will be good at all distances, so this ratio will be close to 100%. Then if the distance/actuator command relationship changes with time, the contrast will get lower.

FIG. 4B shows a possible evolution of the actuator command for a linear actuator as described in FIG. 2B, during the lifetime of the product; In this case the command to reach Distance 1 decreases with time and the command to reach Distance 2 increases. So, if no recalibration is applied, the contrast of images taken at Distance 1 and Distance 2 becomes lower, as well as some intermediate distances. If this evolution is predicted by the actuator supplier (for example the liquid lens as previously described), recording the evolution of the contrast at different distances can be translated into a recalibration of the actuator commands. As an example, the graph shown on FIG. 4B triggers a decrease of actuator command C1 and an increase of C2. To maximize the efficiency and eliminate errors, this recalibration should be applied when a significant amount of data has been recorded (typically at least 1000 points). That way, the averaging of all situations gives a general tendency rather than the effect of a small number of decodings. When a given threshold is reached (for example, a ratio of (contrast>80%)/(contrast>20%) lower than 75% for one distance zone), the recalibration process may be launched and the decoding number values are reinitialized.

Although some embodiments related to barcode reader applications have been described, the invention according the first aspect may also apply to other imaging systems equipped with a distance measurement device, included but not limited to camera modules for mobile phones, Personal Digital Assistants, webcams, medical or industrial endoscopes, machine vision image capture devices, fingerprint or iris recognition systems.

Calibration Method According to the Second Aspect of the Invention

According to a second aspect, the invention is directed to a real time calibration method that can also be refer to an in the field calibration method using a specific calibration system implemented in the imaging system. The invention according to the second aspect of the invention encompasses different embodiments of a method of calibration in the field of an open loop variable focus imaging system and also imaging systems using such.

Figure 1A:
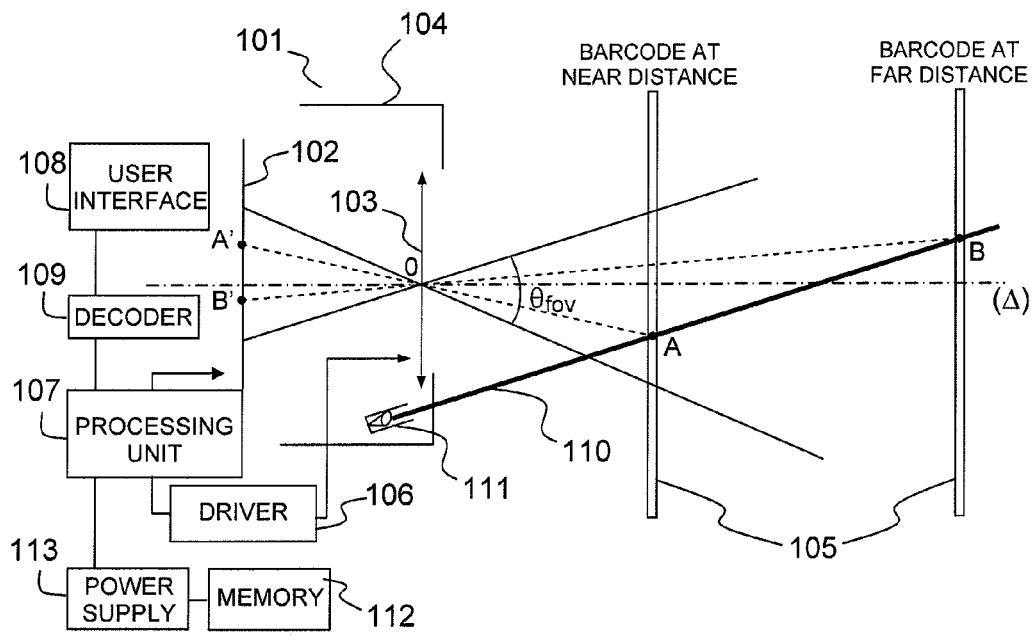
FIG. 1A is a schema of a bar code reader according to the prior art.
Figure 1B:
FIG. 1B is a graph showing the relationship between the actuator command and the focusing distance when the actuator is a liquid lens, according to the prior art.

The imaging system may comprise a sensor and a lens arrangement with an electrically controlled optical device, for example a liquid lens, for adjusting an optical parameter such as focus and/or tilt of said electrically controlled optical device. This optical parameter may be adjusted as a function of an external measured parameter, for example a distance measurement in the case of a variable focus image capture system (e.g., autofocus system or barcode reader as described on FIG. 1A), or a tilt measurement, for example in an optical image stabilization system. The imaging system may further comprise a driver for applying a predetermined electrical signal to the electrically controlled optical device which is a function of the external measured parameter.

The calibration system may be integrated in the imaging system, and includes a light emitting system which forms an image of a light source on the sensor of the imaging system, through the lens arrangement of said imaging system. For example, the light emitting system comprises light source and a lens to form a quasi collimated beam, and means to form the image of the light source in the field of view of the imaging system through the lens arrangement of said imagery system. It further comprises processing means (for example an ISP) to analyze the image of the light source that will be formed in a given sub area of the sensor, different from the area where the laser spots are formed.

The centroid of the image of the light source image as well as the shape of the image may give all the information to determine the optical parameter, for example the focus or the tilt of electrically controlled optical device, e.g. a variable focal length liquid lens and/or an image stabilization liquid lens, and thus allows calibrating the device at any time.

In a preferred embodiment, the light emitting system emits a quasi collimated beam with a given astigmatism, for example using an astigmatic lens. This results in an image whose shape varies as a function of the optical power of the imaging system. Analysis of the image thus enables to determine the effective optical power of the imaging device and calibration of the electrically controlled optical device when the optical parameter to be adjusted is focus. Although analysis of the image will be described using astigmatism, other aberrations may be used that generate images, the analysis of which enabling to determine the optical power of the system.

Figure 5A:
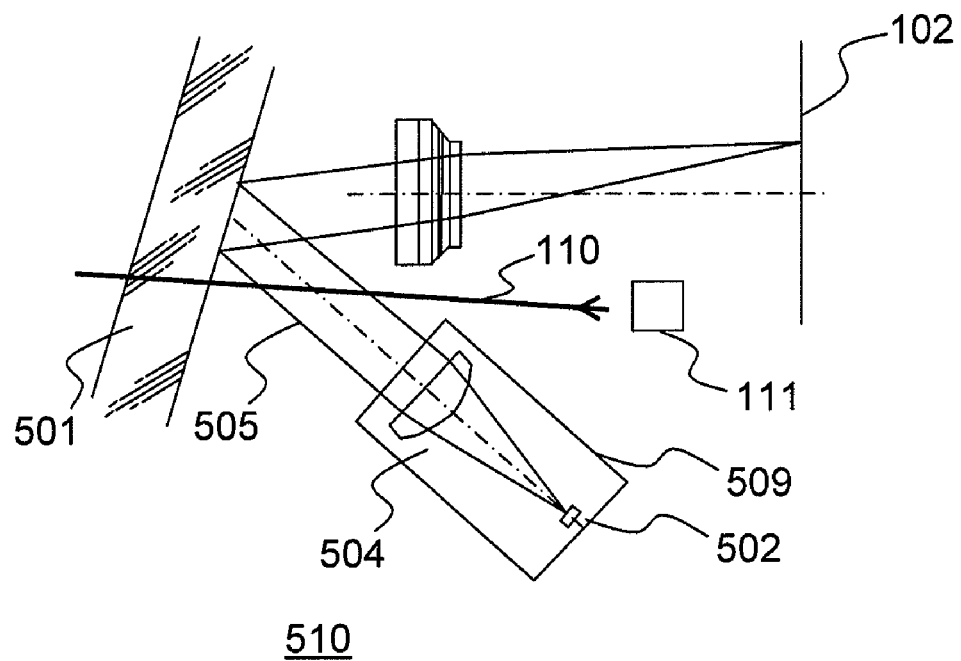
FIG. 5A is a schematic drawing showing the calibration system implemented in an imaging system, for example a barcode reader using a liquid lens as electrically controlled focal length optical device, according to an embodiment of the second aspect of the invention.

FIG. 5 illustrates the real time calibration method and imaging system using such according to one embodiment of this second aspect of the invention. FIG. 5A illustrates an imaging system embodiment used for example in a bar code reader as shown on FIG. 1A. From the barcode reader illustrated in FIG. 1A, only the sensor 102, the lens arrangement 103, the laser source 111 and the emitted laser beam 110 for the distance measurement are represented in FIG. 5A. For the barcode application, since most of the scanners are made from a so called "scan engine" enclosed in a specific packaging, a window 501 is generally placed in front of the scan engine to protect it and seal the entire core of the system such that the system can be used in relatively high demanding industrial environment. Such window is generally tilted with respect to the laser beam 111 in order to avoid parasitic reflections that would lead to a poor performance device. In the described embodiment, the imaging system comprises the sensor 102, the optical lens arrangement 103 that comprises an electrically controlled optical device (not represented on FIG. 5A), for example a liquid lens allowing adjusting the focus of the device, and a calibration system comprising a light emitting system 509, the window 501 and a processing unit (not shown) for analysing images of the light emitting system formed on the image sensor 102. The liquid lens is controlled by a driver (not shown in the FIG. 5A) applying electrical signals, for example different voltages to the liquid lens. The light emitting system 509 comprises for example a LED 503 and a single plastic lens 504 with a given astigmatism, and emits a light beam 505 that is reflected by the window into the field of view 510 of the imaging system. Beam 505 is for example a quasi collimated beam having 5 to 1 dioptres of astigmatism and the window tilt can for example range from 10 to 30 degrees with respect to the optical axis of the imaging system (Δ).

Figure 5B:
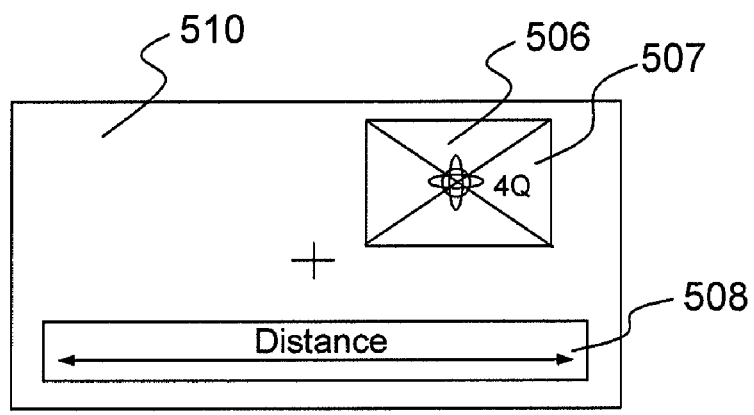
FIG. 5B is a drawing illustrating the display of the image formed on the sensor during a calibration method according to the second aspect of the invention, and used in a imaging system as illustrated in FIG. 5A.

As shown on FIG. 5B, the image 506 of the quasi collimated light source appears in the field of view 510 of the imaging system when the LED is switched on. The image 506 of the quasi collimated light source appears in a zone 507 of the field of view 510 while the image of the laser source used for the distance measurement appears in separate zone 8. In a further embodiment, the zones 507 and 508 can be at least partially superimposed. In that case, the distance measurement and the calibration may be made alternatively. The quasi collimated light source being stable with respect to the imaging system, an image analysis of its shape as well as its centroid position can be used to perform calibration of the focusing optical device whenever it is required. For example, calibration can be achieved on request by a user, when in sleep mode, or periodically at a fixed time.

Figure 6A:
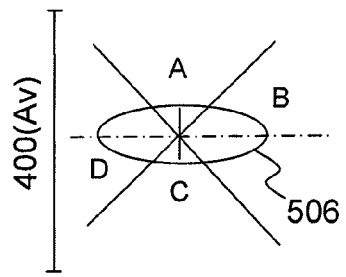
FIGS. 6A to 6G show, for different applied voltages, the spot shape of the images of an astigmatic light source formed on the sensor that can be used in the calibration method according to embodiments of FIGS. 5A and 5B and according to the second aspect of the invention.
Figure 6B:
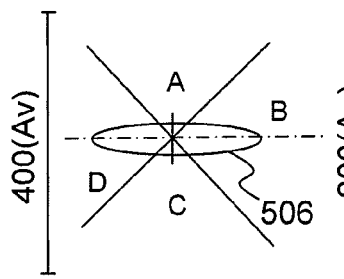
Figure 6C:
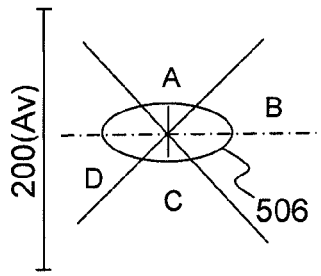
Figure 6D:
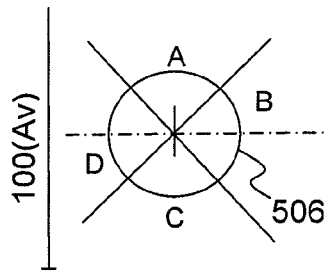
Figure 6E:
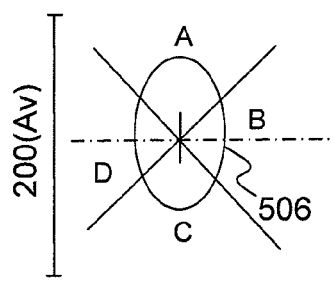
Figure 6F:
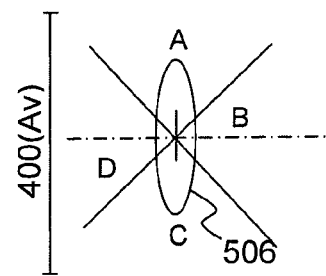
Figure 6G:
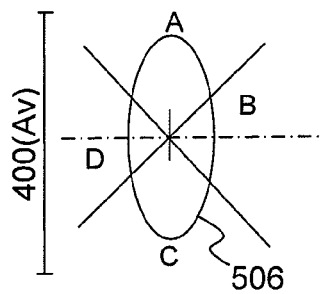

One embodiment of the calibration method according to the second aspect if the invention is now described, in relation to FIGS. 6A to 6G and FIG. 7. FIGS. 6A to 6G represent the images 506 of the quasi collimated beam on the sensor of the imaging system reflected through the window. Depending on the voltage applied to the liquid lens, the shape and the orientation of the spot change from a thick vertical line to a horizontal line with an intermediate focus position where the image spot is round (FIG. 6D). The quasi collimated beam has a known astigmatism (in this example, 10 dioptres) and the imaging system is focused at infinity when the optical power of the liquid lens is 0 dioptres, corresponding for example to an applied voltage of about 40 Volts. In this example, FIG. 6A corresponds to the image of the quasi collimated beam when the nominal value of the optical power of the liquid lens is (−5) dioptres, corresponding to an applied voltage $V_A$. FIG. 6B corresponds to the image of the quasi collimated beam when the nominal value of the optical power of the liquid lens being 0 dioptre, corresponding to an applied voltage $V_B$=39V. Image 506 of the quasi collimated beam of FIG. 6B corresponds to the best focus in horizontal direction. FIG. 6C corresponds to the image of the quasi collimated beam when the nominal value of the optical power of the liquid lens is around 2.5 dioptres, corresponding to an applied voltage $V_C$. FIG. 6D corresponds to the image of the quasi collimated beam when the nominal value of the optical power of the liquid lens is 5 dioptres, corresponding to an applied voltage $V_D$, and corresponds to the so-called best focus. FIG. 6E corresponds to the image of the quasi collimated beam when the nominal value of the optical power of the liquid lens is 7.5 dioptres, corresponding to an applied voltage $V_E$. FIG. 6F corresponds to the image of the quasi collimated beam when the nominal value of the optical power of the liquid lens is 10 dioptres, i.e. 10 cm object distance, corresponding to an applied voltage $V_F$, and corresponds to the best focus in vertical direction. FIG. 6G corresponds to the image of the quasi collimated beam when the nominal value of the optical power of the liquid lens is 12.5 dioptres, corresponding to an applied voltage $V_G$). The calibration method comprises the determination of the exact corresponding optical power as a function of the applied voltage, and the update of the parameters of the pre registered function. To achieve this, the image area is split in four different quadrants of same size, named respectively A, B, C and D on FIGS. 6A to 6G. The energy collected in the different quadrants is estimated and enables to determine the optical power of the system, and thus the optical power of the liquid lens. Known algorithms of the art are used to determine the optical power from an output signal issued from the energy collected in the quadrants. For example, the output signal used to determine the optical power is the function $F(V)=(E_A+E_C)-(E_B+E_D)$ where $E_A$, $E_B$, $E_C$ and $E_D$ are the energies collected respectively in the quadrants A, B, C and D and V is the applied voltage to the liquid lens.

Figure 7:
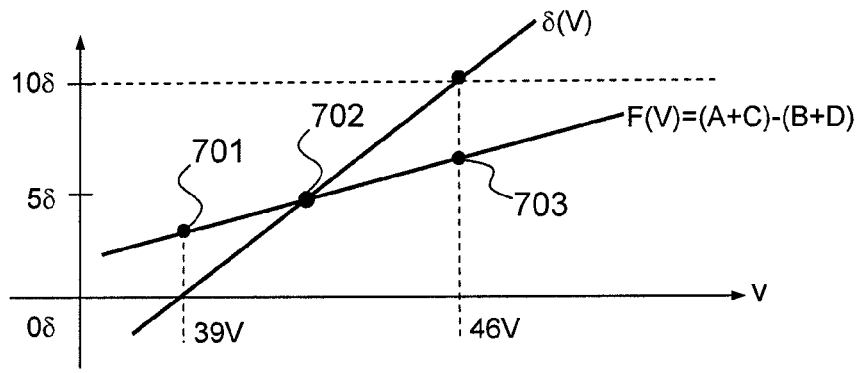
FIG. 7 shows examples of response curves resulting from the image processing of the images shown on FIGS. 6A to 6G, used in the calibration method according to the same embodiment as in FIGS. 6A to 6G and according to the second aspect of the invention.

FIG. 7 is a graph illustrating two response curves, F(V), as defined above, and $\delta(V)$, which is the response curve of the liquid lens and which can be derived from F(V) since the quasi-collimated beam astigmatism value is predefined and F(V) is function of the optical power of the liquid lens. From determining F(V) for at least two values of the voltage, it is thus possible to determine the response curve of the liquid lens. In the example shown on FIG. 7, points 701, 702, 703 on the measured F(V) when the voltage applied to the liquid lens corresponds to respectively $V_B$, $V_D$ and $V_E$ as refer on FIGS. 6A to 6G.

Figure 8A:
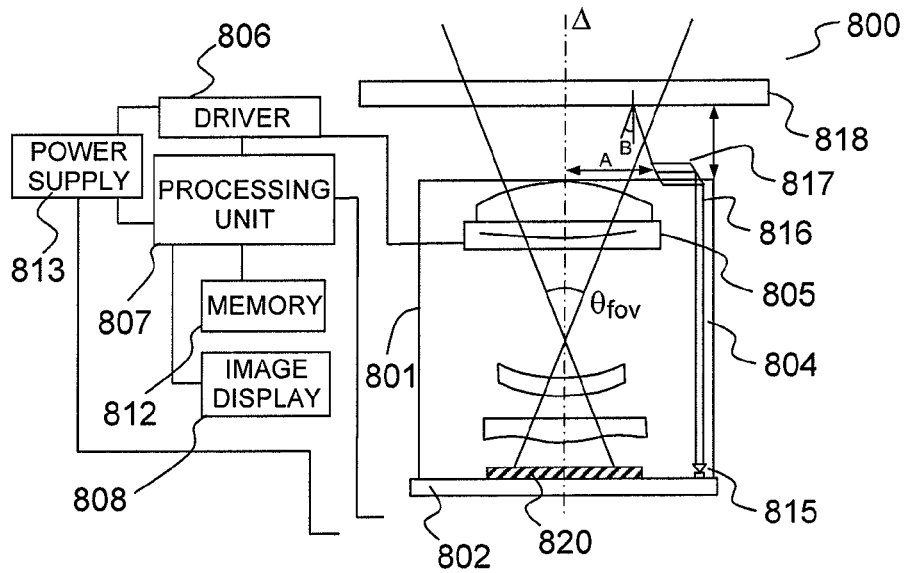
FIGS. 8A and 8B are drawing illustrating a calibration method and an imaging system using such, for example an imaging system for implementation in a mobile phone device, according to another embodiment of the second aspect of the invention.

FIG. 8A illustrates the application of the real time calibration method and imaging system using such in a further embodiment according to the second aspect of the invention. Such an embodiment is particularly interesting for very compact imaging systems, for example a mobile phone device, where real estate is expensive.

The imaging system 800 described on FIG. 8A is for example an autofocus imaging device comprising a camera module 801 characterized by an optical axis ($\Delta$) and a field of view $\theta_{FOV}$, with a sensor 802 and a lens arrangement 803, settled in a lens mount 804, that includes fixed lenses and an electronically controlled optical device 805, for example a liquid lens, for adjusting the focal length. The system further comprises a driver 806 to control the electronically controlled optical device 805, a processing unit 807 linked to an image display 808 and to a memory unit 812 in which the calibration parameters, such as a look-up table, are stored. A power supply 813 provides electrical power to the different units.

In such an embodiment, the light source 815 of the calibration system may be directly mounted on the sensor substrate 802 and a collimation lens is placed in the lens mount 804. The quasi collimated beam generated is located in one of the corner of the lens mount without increasing the print of the camera module assembly. The protective window 818 being close to the camera module (CM) nose and the quasi collimated beam being mainly parallel to the optical axis of the imaging system in such embodiment, a deflection system 817 can be required. The deflection system 817 can be a prism or a mirror that will deflect the beam onto the field of view of the imaging system.

In a further embodiment according to the second aspect of the invention, the calibration method and imaging system can also be applied to optical image stabilisation in imaging systems using an electrically controlled actuator to adjust the tilt. Such an embodiment is similar to the one described in FIG. 8A, except that the electrically controlled actuator is used to adjust the tilt of the optical axis of the imaging system. Such an imaging system having optical image stabilisation function is particularly interesting in mobile phones where image stabilisation is a critical parameter to get a good quality of image. The actuator may be controlled according to the motion of the imaging system measured using a motion detector, such as a gyrometer (gyroscope sensor) for example. The electrically controlled device is arranged to shift an image formed on said image sensor in response to a motion detected by the motion detector.

Advantageously, the electrically controlled device for adjusting the tilt is a liquid lens with a plurality of electrodes which can be controlled independently to selectively deform the liquid-liquid interface and introduce the desired tilt. Advantageously, a liquid lens as described for example in European patent application EP2009468 (EP 07301180.1) in name of the applicant can be used. It comprises a chamber with first and second immiscible liquids contacting each other at a liquid-liquid interface, the first liquid being an insulating liquid and the second liquid being a conducting liquid. It further comprises a first electrode in contact with the second liquid and a second electrode insulated from the first and second liquids by an insulating layer and formed of a conductive polymer material. The curvature of said liquid-liquid interface is controllable by application of a voltage between the first and second electrodes. A plurality of contact points on said second electrode are arranged to receive an independent voltage for controlling different parts of said liquid-liquid interface and introduce a desired tilt.

Figure 8B:
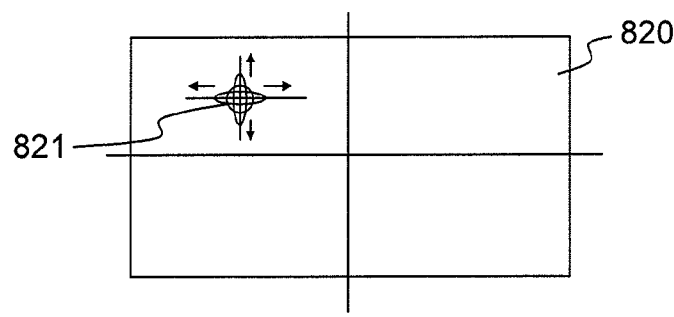

As shown on FIG. 8B, by calculating the displacement of the centroid of the image of the source on the sensor, it is possible to determine the tilt introduced by the liquid lens as function of the voltage applied, and thus, it is possible to calibrate the liquid lens response curve in a close-loop Optical Image Stabilization (OIS) based liquid lens. A major advantage is the relaxing of the constraints in the specification of the liquid lens. Indeed, if the specification slightly changes over its life time, calibration is made possible on the field, in an automatic process.

As mentioned before, the FIG. 8A shows specific imaging system embodiments, particularly well suited to mobile phone application for example, in which the camera module compactness is very high. The quasi collimated source may be located in a corner of the camera module holder, and a LED may be mounted on the same substrate as the sensor such that a beam is reflected back to the imaging system field of view through a double reflection mirror or prism. The position of the light source and the substrate, the position of the prism or mirror 817 relative to the protecting window 818 and the deflection angle of said prism or mirror need to be arranged such that the quasi collimated beam gets into the field of view of the camera module. For example, let us consider a camera module with a total angular field of view of 66°. The distance D between the window and the nose of the Camera Module, the distance A between the quasi collimated beam and the optical axis $\Delta$, and the angle B of the last reflection of the collimated beam on the prism or mirror with respect to the optical axis of the lens module are related by the formula $TAN(B)=(A-0.25)*0.5/D$. For example, for D=2 mm, A=1 mm, B must be around 20°.

One advantage of the calibration method according to a second aspect of the invention as described above is that it can be performed in real time or quasi real time, and thus, can also take into account the slight of the performances of the electrically controlled device, e.g., the liquid lens, due to the temperature.

Although embodiments related to barcode reader and mobile phone applications have been described, the invention according the second aspect may also apply for other applications such as imaging into Personal Digital Assistants, webcams, medical or industrial endoscopes, machine vision image capture devices, fingerprint or iris recognition systems.

While the disclosure has been presented with respect to a limited number of embodiments, those skilled in the art, having benefit of this disclosure, will appreciate that other embodiments may be devised which do not depart from the scope of the present disclosure. Accordingly, the scope of the invention should be limited only by the attached claims.

What is claimed is:

1. A method for calibration in the field of an open loop variable focus imaging system, said imaging system comprising a sensor, a lens arrangement with an electrically controlled focal length optical device for adjusting the focus as a function of a distance measurement of an object to be imaged, a driver for applying a predetermined electrical signal to the electrically controlled optical device, said signal being related to the measured distance by a function comprising pre-recorded parameters, the method comprising:
for at least two distances, determining for each distance the value of the electrical signal to be applied to get a best image contrast measurement of the object to be imaged positioned at said distance; and
updating the pre-recorded parameters of the function between the electrical signal to be applied and the measured distance using the values associated with the at least two distances.

2. The method of claim 1, wherein determining said value comprises applying an electrical signal to the electrically controlled focal length optical device over a given range and analyzing an image formed for each signal applied, until the best image contrast measurement is obtained.

3. The method of claim 2, wherein determining said value comprises a coarse search, where the electrical signal is applied with large steps over a whole range, and a fine search, where the electrical signal is applied with small steps over a limited range.

4. The method of claim 1, wherein the electrically controlled focal length optical device is a liquid lens and the electrical signal to be applied is a voltage signal.

5. The method of claim 4, wherein the function between the measured distance and a voltage to be applied to the liquid lens is quasi linear, and wherein updating the pre-recorded parameters of said function comprises determining two values of the voltage to be applied to get the best image contrast measurement of an image of an object positioned at the at least two distances.

6. A method for calibration in the field of an open loop variable focus imaging system, said imaging system comprising a sensor, a lens arrangement with an electrically controlled focal length optical device for adjusting the focus as function of a distance measurement of an object to be imaged, a driver for applying a predetermined electrical signal to the electrically controlled optical device, said signal being related to the measured distance by a function comprising pre-recorded parameters, the method comprising:
recording, over a life time of the imaging system, values of contrast image measurements for images of an object as a function of the distance of said object;
determining when a significant loss of contrast has occurred using the recorded values; and
applying a correction in the pre-recorded parameters of the function as a function of said loss of contrast.

7. An open loop variable focus imaging system comprising:
a sensor;
a lens arrangement with an electrically controlled focal length optical device for adjusting focus as a function of a distance measurement of an object to be imaged;
a driver for applying a predetermined electrical signal to the electrically controlled optical device, wherein the electrical signal is related to the distance measurement by a function comprising pre-recorded parameters stored in a memory unit; and
a processing unit comprising:
image analyzing means for determining, for at least two distances, the value of the electrical signal to be applied to get a best image contrast measurement of the object to be imaged positioned at said distance, and
calculating means for updating the pre-recorded parameters of the function between the electrical signal to be applied and the measured distance using the values determined for the at least two distances.

8. An open loop variable focus imaging system comprising:
a sensor;
a lens arrangement with an electrically controlled focal length optical device for adjusting the focus as a function of a distance measurement of an object to be imaged;
a driver for applying a predetermined electrical signal to the electrically controlled optical device, wherein the electrical signal is related to the distance measurement by a function comprising pre-corded parameters stored in a memory unit; and
a processing unit comprising:
image analyzing means for recording, over a life time of the imaging system, values of contrast image measurements for images of an object as function of the distance of said object, and
calculating means for determining when a significant loss of contrast has occurred using the recorded values, and for applying a correction in the pre-recorded parameters of the function as a function of said loss of contrast.

9. A method for calibration in the field of an imaging system comprising a sensor, a lens arrangement with an electrically controlled optical device for adjusting a given optical parameter as a function of an external measured parameter, a driver for applying a predetermined electrical signal to the electrically controlled optical device, wherein the electrical signal is related to the external measured parameter by a function comprising pre-recorded parameters, the method comprising:
providing a calibration system with a light emitting system to form an image of a light source on the sensor of the imaging system through the lens arrangement of said imaging system;
analyzing the image of the light source formed on the sensor for at least two values of the applied electrical signal on the electrically controlled optical device;
determining, for each of the at least two values of said applied signal, the value of the optical parameter from the analysis of the image formed on the sensor; and
updating the pre-recorded parameters of the function between the electrical signal to be applied and the external measured parameter using the at least two values.

10. A method of claim 9, wherein the electrically controlled optical device is an electrically controlled focal length device, the light emitting system is provided to form an image with a given astigmatism, wherein the analysis of a shape of the image enables to determine a focus of the electrically controlled optical device for each applied electrical signal.

11. The method of claim 10, wherein analyzing the shape of the image comprises measuring the energy in four quadrants of the image sensor, the quadrants having the same size and being centred on a centroid of the image of the light source.

12. The method of claim 10, wherein the electrically controlled focal length optical device is a liquid lens and the electrical signal to be applied is a voltage signal.

13. The method of claim 11, wherein the adjustable optical parameter is tilt, and the external measured parameter is a motion of the imaging system, the method further comprising analyzing the images of the light source formed on the sensor by calculating the displacement of the centroid of each of the images formed for the at least two values of the applied electrical signal.

14. The method of claim 13, wherein the electrically controlled optical device is a liquid lens with a plurality of electrodes and the electrical signal to be applied is a voltage signal.

15. An imaging system comprising:
a sensor,
a lens arrangement with an electrically controlled optical device for adjusting a given optical parameter as function of an external measured parameter;
a driver for applying a predetermined electrical signal to the electrically controlled optical device, said signal being related to the external measured parameter by a given function;
a calibration system to determine the function between said electrical signal and the external measured parameter, comprising:
a light emitting system to form an image of a light source on the sensor of the imaging system through the lens arrangement of said imaging system, and
a processing unit with image analyzing means to analyze the images of the light source formed on the sensor for at least two values of the applied electrical signal, and calculating means to determine a value of the optical parameter for each applied electrical signal.

16. The imaging system of claim 15, wherein the adjustable optical parameter is focal length, and the external measured parameter is a distance measurement, and wherein the light emitting system is provided to form an image of the light source with a given astigmatism, and the image analyzing means is enabled to analyze a shape of the image to determine a focus of the electrically controlled device as a function of the applied electrical signal.

17. The imaging system of claim 16, wherein the electrically controlled optical device is a liquid lens.

18. The imaging system of claim 16, wherein the light emitting system comprises a light source, a lens to form a quasi collimated beam with said given astigmatism, and reflection means to reflect said quasi collimated beam on the sensor of the imaging system.

19. The imaging system of claim 18, wherein the imaging system comprising a protective window with a given inclination, and the reflection means are formed by said protecting window.

20. The imaging system of claim 18, wherein the sensor is arranged on a substrate, the light source is arranged on the same substrate, and the reflection means comprise a double reflection mirror or a prism.

21. The imaging system of claim 20, wherein the imaging system comprises a protective window, and the reflection means further comprise said protecting window.

22. The imaging system of claim 15, wherein the adjustable optical parameter is tilt, and the external measured parameter is a motion of the imaging system, wherein the image analyzing means is enabled to analyze a displacement of the image to determine the tilt of the electrically controlled device as function of the applied electrical signal.

* * * * *